United States Patent [19]
Todd et al.

[11] 4,395,260
[45] Jul. 26, 1983

[54] DRIP CHAMBER

[75] Inventors: Robert J. Todd, Salt Lake City; Gordon S. Reynolds, Bountiful, both of Utah

[73] Assignee: Sorenson Research Co., Inc., Salt Lake City, Utah

[21] Appl. No.: 269,937

[22] Filed: Jun. 1, 1981

[51] Int. Cl.³ .............................................. A61M 5/16
[52] U.S. Cl. .................... 604/122; 604/252; 210/188; 210/927
[58] Field of Search .......... 128/214 R, 214 C, 214 Z; 210/927, 131, 398, 436, 188; 604/122, 251–252

[56] References Cited

U.S. PATENT DOCUMENTS

| | | | |
|---|---|---|---|
| 3,030,954 | 4/1962 | Thornton | 128/214 C |
| 3,311,268 | 3/1967 | Fields | 128/214 C X |
| 3,521,635 | 7/1970 | Koehn | 128/214 C |
| 3,677,242 | 7/1972 | Shaye | 128/214 C |
| 3,935,111 | 1/1976 | Bentley | 210/927 X |
| 4,056,100 | 11/1977 | Noiles | 128/214 C |

FOREIGN PATENT DOCUMENTS 1069834 11/1959 Fed. Rep. of Germany ... 128/214 C

*Primary Examiner*—Dalton L. Truluck
*Attorney, Agent, or Firm*—Rich D. Nydegger; Robert S. Beiser

[57] ABSTRACT

An apparatus and method for effectively eliminating the risk of introducing air bubbles into a fluid delivery system such as to administer parenteral fluids to a patient. The apparatus comprises a baffle positioned within a drip chamber for deflecting fluid expelled from a fluid resistor in order to eliminate turbulence and the formation of micro-bubbles during rapid filling or flushing of the fluid delivery system. The drip chamber also comprises a filter membrane positioned across the outlet of the drip chamber. The filter membrane is attached to a filter carrier assembly which enables the filter membrane to be momentarily displaced so that air bubbles trapped beneath the filter membrane may escape.

18 Claims, 12 Drawing Figures

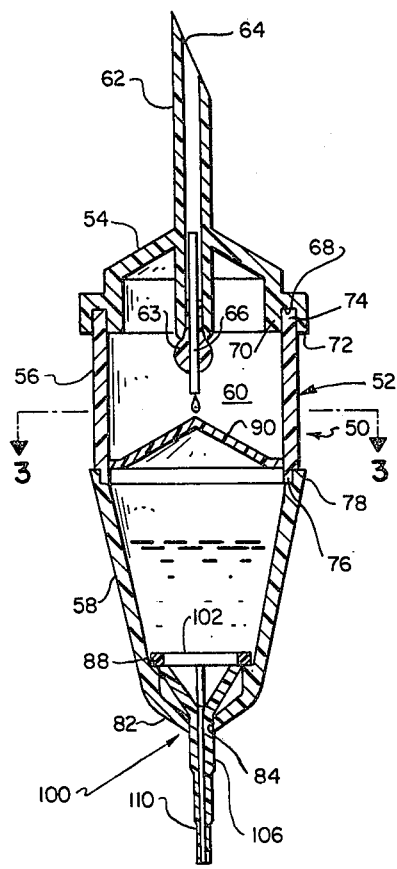
Fig. 1
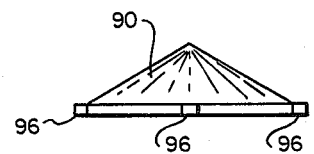
Fig. 2
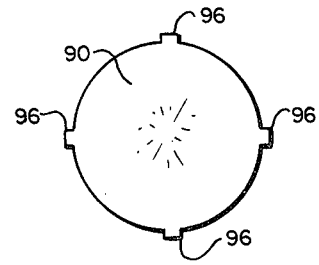
Fig. 2a
Fig. 3
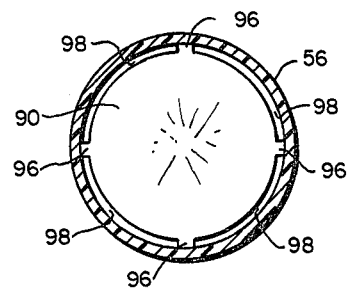
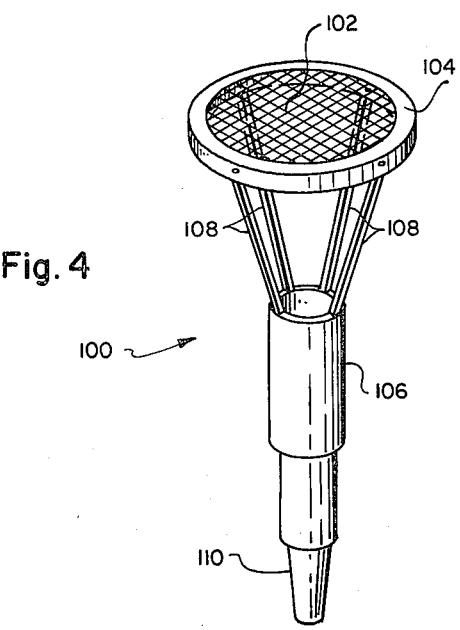
Fig. 4
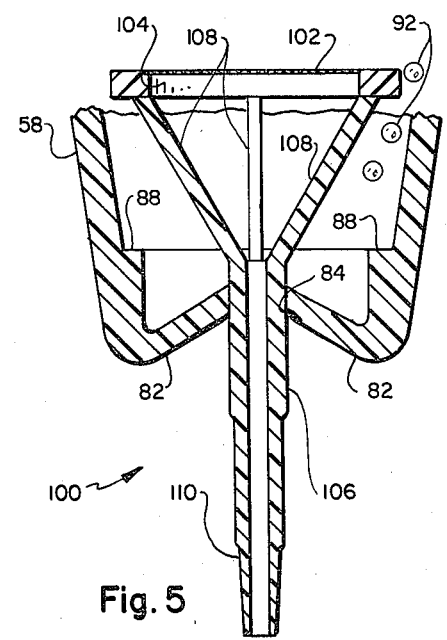
Fig. 5

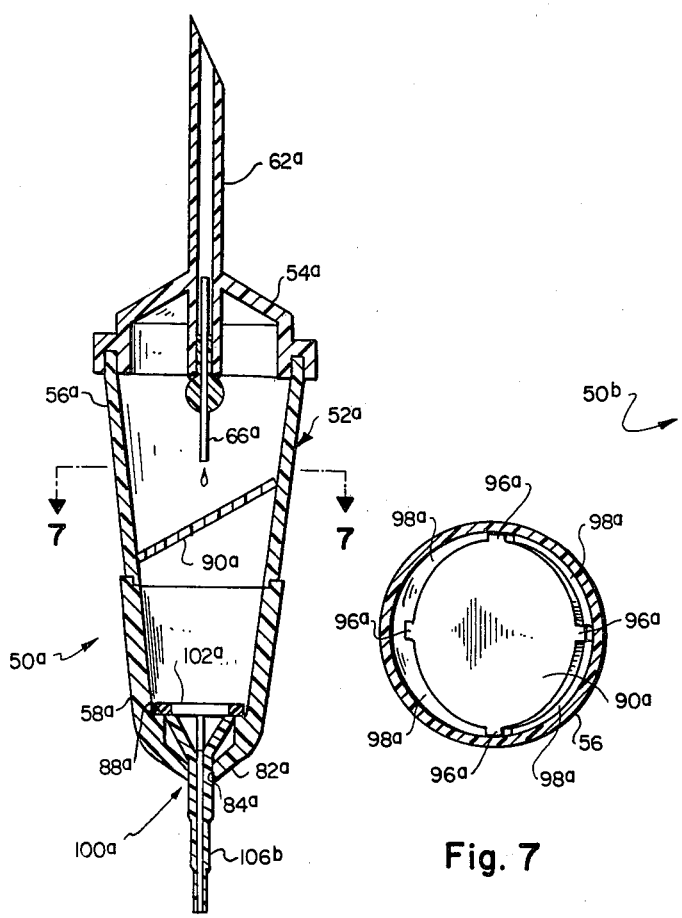
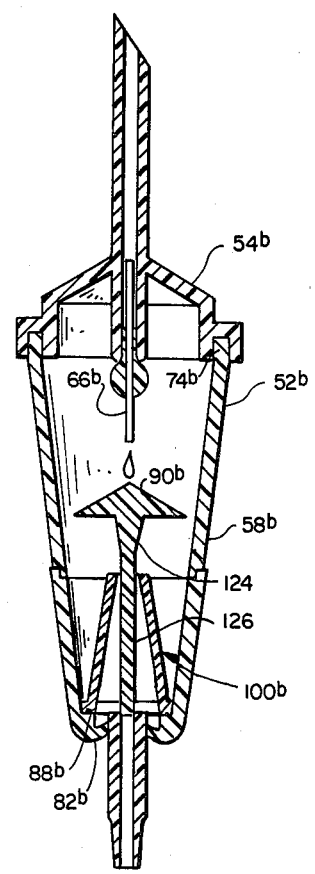
Fig. 6
Fig. 7
Fig. 8
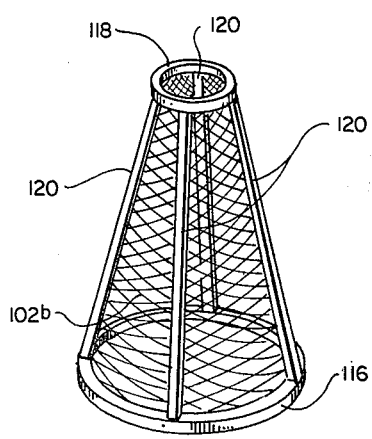
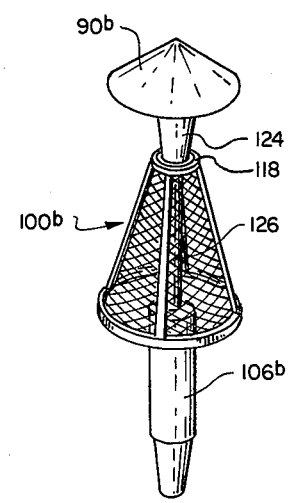
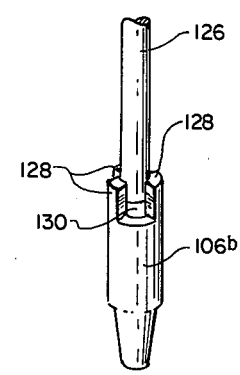
Fig. 9
Fig 10
Fig. 11

DRIP CHAMBER

BACKGROUND

1. Field of the Invention

The present invention relates to an improved drip chamber, and more particularly, to a drip chamber provided with a bubble trap filter that is designed to prevent the introduction of air bubbles into a fluid delivery system such as used for the administration of parenteral fluids to a patient or such as used for continuous flushing of a central arterial blood pressure monitoring system.

2. The Prior Art

The use of drip chambers as a component part of fluid delivery systems to administer parenteral fluids to a patient or such as used to continuously flush a central arterial blood pressure monitoring system has long been known in the art. Conventional drip chambers typically consist of a fluid resistor that is suspended and enclosed in a transparent chamber. The transparent chamber collects the fluid expelled from the fluid resistor, and by visually observing the rate at which drops of fluid fall from the fluid resistor the approximate rate of infusion into the patient may be determined, as well as verifying that fluid is in fact being infused into the patient.

In the past, a chronic problem has been the risk of introducing air bubbles into the fluid delivery system by reason of the drip chamber. Typically, this problem occurs in several ways. When the fluid delivery system is initially filled or when a large quantity of the infusion fluid must be rapidly washed through the delivery system, a high velocity jet of fluid is expelled from the fluid resistor in the drip chamber. The high velocity jet of fluid causes a venturi effect such that air is pulled with the high velocity jet of fluid and is injected into a fluid reservoir that collects at the bottom of the drip chamber. The air injected into the fluid reservoir forms numerous micro-bubbles which subsequently flow out of the drip chamber and into the tubing and catheter of the fluid delivery system. These air bubbles can become entrapped in the drip chamber and then later injected into the catheter delivery system.

Introduction of air bubbles into the fluid delivery system can be extremely hazardous. For example, it is well known that intravenous introduction of air bubbles may result in an embolism which may block a blood vessel. This can be extremely dangerous to a patient and in some cases way even result in death. Thus, the problem which is faced is how to eliminate the introduction of air bubbles into the tubing and catheter of the fluid delivery system.

Although various attempts to solve this problem have been made by those skilled in the art, to date there has not been devised an apparatus and method that has fully succeeded in achieving a saatisfactory solution to this problem.

For example, one typical attempt to solve the problem has been to place a fine mesh filter screen at the bottom of the drip chamber. This prior art technique has several significant drawbacks. For example, from time to time it may be necessary to rapidly inject fluid through the delivery system. When this occurs, as previously described, a high velocity jet of fluid is expelled through the fluid resistor which strikes the fluid reservoir contained in the drip chamber. The venturi effect and turbulence caused by the high velocity jet of fluid creates a large number of micro-bubbles that can be driven right through the screen that is placed at the bottom of the drip chamber.

Another serious drawback with the prior art approach to the solution of this problem is that when initially filling the fluid delivery system, large air bubbles are almost always trapped under the filter screen placed at the bottom of the drip chamber. The large air bubbles which are trapped beneath the filter screen are almost impossible to remove once the fluid delivery system has been filled. Thus, the existence of air bubbles trapped beneath the filter screen are a further factor which may cause concern on the part of medical technicians or other personnel using the fluid delivery system for the administration of parenteral fluids.

In summary, although the use of drip chambers as a component part of fluid delivery systems has long been recognized as an important way to verify the continuous infusion of fluid to a patient and to verify the approximate rate of infusion, there has not yet been devised an effective way of minimizing risk to the patient by eliminating the introduction of micro-bubbles into the fluid delivery system during rapid flushing of the system. Nor has there been devised an effective way to eliminate the air bubbles that are typically entrapped beneath the filter screen, such as currently used in most types of prior art drip chambers.

BRIEF SUMMARY AND OBJECTS OF THE INVENTION

The present invention is directed to an apparatus and method for effectively eliminating the risk of introducing air bubbles into a fluid delivery system such as used to administer parenteral fluids to a patient. The apparatus comprises a baffle positioned within a drip chamber and a filter membrane positioned across the outlet of the drip chamber. The baffle deflects the fluid expelled from the fluid resistor in order to eliminate turbulence and the formation of micro-bubbles during rapid filling or flushing of the fluid delivery system. The filter membrane is attached to a filter carrier assembly which enables the filter membrane to be momentarily displaced so that air bubbles trapped beneath the filter membrane may escape.

It is therefore a primary object of the present invention to provide an improved apparatus and method for effectively eliminating the risk of introducing air bubbles into a fluid delivery system.

Another object of the present invention is to provide an improved drip chamber.

A further object of the present invention is to provide a drip chamber with a displaceable filter membrane that may be operated to release air entrapped beneath the membrane.

Another object of the present invention is to provide a drip chamber with a baffle that helps to prevent introduction of micro-bubbles into the system by reducing turbulence when filling or flushing the system.

These and other objects and features of the present invention will become more fully apparent from the following description and appended claims taken in conjunction with the accompanying drawing.

BRIEF DESCRIPTION OF THE DRAWING

FIG. 1 is a cross-sectional view of one preferred embodiment of the present invention;

FIG. 2 is a side elevational view of the baffle element of the embodiment illustrated in FIG. 1;

FIG. 2a is a top plan view of the baffle element of FIG. 2;

FIG. 3 is a cross-sectional view taken along lines 3—3 of FIG. 1;

FIG. 4 is an enlarged perspective view of the filter membrane carrier of the embodiment illustrated in FIG. 1;

FIG. 5 is an enlarged partial cross-sectional view illustrating displacement of the filter membrane carrier assembly to release entrapped air bubbles;

FIG. 6 is a cross-sectional view of a second embodiment of the present invention;

FIG. 7 is a cross-sectional view taken along lines 7—7 of FIG. 6;

FIG. 8 is a cross-sectional view of a third embodiment of the present invention;

FIG. 9 is an enlarged perspective view of the filter membrane of the embodiment illustrated in FIG. 8;

FIG. 10 is a perspective view of the baffle element and filter membrane carrier assembly of the embodiment illustrated in FIG. 8; and FIG. 11 is an enlarged perspective view of portions of the baffle element and filter membrane carrier assembly illustrated in FIG. 10.

DETAILWED DESCRIPTION OF THE PREFERRED EMBODIMENTS

With reference to FIG. 1, the drip chamber of the present invention is illustrated and generally designated at 50. Drip chamber 50 has a generally cylindrical housing 52 which comprises an inlet cover 54, a rigid housing section 56 and a flexible housing section 58. Contained within housing 52 is a chamber 60.

Inlet cover 54 is provided with an inlet tube 62 for communicating infusion fluids from a fluid source (not shown) into chamber 60. The distal end 64 of inlet tube 62 is typically beveled and sharpened for ease of insertion into a bag or bottle which serves as the source of the infusion fluid. Bonded to the other end of inlet tube 62 is a plug 63 which carries a diametrally reduced metal tube 66. As is customary, tube 66 may be sized to accomodate a selected rate of fluid infusion at a given pressure level. As further illustrated in FIG. 1, inlet cover 54 has an annular recess 68 formed between flanges 70 and 72. The annular recess 68 receives the upper margin 74 of rigid housing section 56 in mating relationship. Cover 54 may be permanently bonded to the upper margin 74 of housing section 56 by any conventional method such as solvent bonding or ultrasonic welding.

Rigid housing section 56 is preferably fashioned from clear, plastic material so that droplets issuing from tube 66 are clearly visible. Housing section 56 is also provided with a short extending flange 76 at its lower end for receiving the upper margin 78 of flexible housing section 58 in press fit relationship. Housing sections 56 and 58 are permanently bonded at flange 76 by any suitable bonding method.

With further reference to FIG. 1, flexible housing section 58 tapers inwardly from top to bottom and forms a reservoir for collecting the fluid expelled from tube 66. The bottom portion 82 of housing section 58 presents a concave interior surface that terminates in an aperture 84. Outlet tube 106 is bonded in the aperture 84. Infusion fluid leaves the chamber 60 through the outlet tube 106 and then passes into the tubing and catheter delivery system (not shown) that is inserted into the patient. The interior surface of bottom portion 82 also presents an annular shoulder 88 that is used to support the filter membrane carrier assembly 100, as herinafter more fully described. Housing section 58 is preferably formed of clear, plastic material so that the fluid level within chamber 60 is clearly visible. Housing section 58 may also be provided with annular markings (not shown) for indicating minimum and maximum fill levels.

As previously described, when filling or flushing the fluid delivery system it may be necessary to rapidly expel fluid from the drip chamber 50. This may be done by squeezing the flexible housing section 58 and then releasing it. When released, a partial vacuum will be created so that a high velocity stream of fluid will be expelled from tube 66. The high velocity stream will strike the reservoir of fluid contained in chamber 60, forming numerous micro-bubbles by the venturi action and turbulence caused by the high velocity stream. In order to eliminate this problem, drip chamber 50 is provided with a conically shaped baffle 90 (see FIGS. 1 and 2). Baffle 90 is situated within chamber 60 such that its convex surface faces inlet cover 54 and is axially aligned with the outlet of tube 66. As shown best in FIGS. 2 and 2a, baffle 90 also comprises a plurality of radially spaced flanges 96 which extend outward to engage the interior wall of housing section 56. Baffle 90 is placed within housing section 56 and bonded thereto at the flanges 96. Alternatively, baffle 90 may be molded as an integral part of housing section 56.

With reference to FIG. 3, when baffle 90 is bonded to housing section 56 as described above, long, narrow apertures 98 are formed between the edges of baffle 90 and the interior walls of housing section 56. When the fluid delivery system is initially filled or is rapidly flushed, the high velocity stream of fluid expelled from tube 66 will impinge the convex surface of baffle 90, and will then be channeled to the apertures 98. Thus, rather than directly striking the reservoir of fluid contained in the chamber 60, the high velocity stream is caused to run down the walls of housing section 58 in a smooth sheet. This advantageously counters the venturi effect and turbulence otherwise caused by the high velocity stream, and thus eliminates formation of the numerous micro-bubbles when filling or flushing the fluid delivery system. Obviously, other baffle configurations could be used to accomplish the same result, and baffle 90 is simply one such suitable configuration.

Drip chamber 50 is also provided with a filter membrane carrier assembly 100 (see FIGS. 1 and 4) positioned within chamber 60 at the outlet aperture 84. As shown best in FIG. 4, the filter membrane carrier 100 has a filter membrane 102 which is bonded to a filter carrier ring 104. The mesh size for filter membrane 102 is typically on the order of 15 microns, but may be varied. Ring 104 is rigidly connected to an outlet tube 106 by a plurality of radially spaced support legs 108. The outlet tube 106 is permanently bonded within aperture 84 of housing section 58 so as to provide an outlet passage from chamber 60 to the external tubing and catheter delivery system (not shown). Outlet tube 106 is also provided with a male fitting 110 for ease in coupling to an external fluid line. Tube 106 is bonded to housing section 58 at its upper end so that the resiliency of flexible housing section 58 biases the filter carrier assembly 100 such that filter carrier ring 104 firmly seats on the annular shoulder 88 in fluid-tight relationship, as shown in FIG. 1. Thus, infusion fluid will be forced to pass through the fine mesh filter membrane 102 prior to exiting through tube 106. The filter membrane 102 will preclude particulate matter and larger air bubbles from entering the fluid delivery system.

Frequently, when initially filling the fluid delivery system, air bubbles will become entrapped beneath the filter membrane 102. With the prior art devices, these entrapped bubbles are extremely difficult, if not impossible, to remove. However, with the drip chamber of the present invention, entrapped bubbles are conveniently released from beneath the filter membrane 102 by displacing the filter carrier assembly 100 longitudinally, as shown in FIG. 5. Displacement of the filter carrier assembly 100 is accomplished by grasping outlet tube 106 and pushing inwardly. Since the housing section 58 is made of a flexible or resilient plastic, the bottom 82 of the housing section 58 may be pushed inwardly as shown in FIG. 5, thus unseating the filter membrane from the annular shoulder 88 and allowing the entrapped air bubbles 92 to escape. After the bubbles, which are clearly visible through housing section 58, are released from beneath filter membrane 102, the filter carrier assembly 100 is reseated against shoulder 88 (see FIG. 1).

From the foregoing description, it may readily be appreciated that the apparatus and method encompassed by the present invention effectively solves the problems heretofore experienced with the prior art type drip chambers. And the foregoing description is but one example of an embodiment which is presently preferred as a means of implementing the objects of the invention.

For example, a second embodiment of the present invention is illustrated in FIGS. 6 and 7.

This embodiment is the same as the previously described embodiment of FIGS. 1–5, except for the baffle 90a. In the embodiment of FIG. 6, the baffle 90a is preferably a piece of flat, rigid plastic material having a plurality of radially spaced flanges 96a which extend outward to engage the interior walls of housing 52a. Baffle 90a has an ellipsoidal shape (see FIG. 7) and is oriented at an angle (see FIG. 6) beneath the tube 66a. As in the previously described embodiment, the spaces between baffle 90a, flanges 96a and housing 52a define a plurality of long, narrow apertures 98a. Baffle 90a intercepts the fluid stream issuing from tube 66a and deflects the infusion fluid to the walls of housing 52a. Thus, as described previously, the infusion fluid is caused to flow in a smooth sheet through apertures 98a and down the inside of the walls of housing 52a into the reservoir of fluid collected below.

A third embodiment of the present invention is illustrated in FIGS. 8–11. In this embodiment, the entire housing 52b is constructed of flexible plastic, and is bonded to inlet cover 54b in the manner previously described. The filter membrane carrier assembly 100b is best illustrated in FIGS. 9–11. As shown in FIG. 9, the filter membrane consists of a framework configurated as a truncated cone. The framework has an upper ring 118 that is rigidly attached to and supported by four radially spaced legs 120. Legs 120 are attached at their other end to a diametrally enlarged ring 116 that is permanently attached to the annular shoulder 88b that is formed inside of the flexible housing 52b at its lower portion 82b. Filter screen 102b is supported by the truncated cone framework formed by rings 116 and 118 and support legs 120.

In the embodiment of FIGS. 8–11, the baffle 90b (see FIGS. 8 and 10) is attached to a vertical stem 126. The stem 126 is flared at its upper end 124 so that it may be firmly seated within the ring 118 of the filter membrane. As illustrated best in FIG. 11, the lower portion of stem 126 seats within the upper portion of outlet tube 106b. Outlet tube 106b is provided with three finger-like extensions 128 to which the lower portion of stem 126 is bonded. Between the finger-like extensions 128 are openings 130 through which fluid may pass, as further described below.

With further reference to FIG. 8, it will be seen that the baffle 90b is diametrally reduced with respect to the inside diameter of the flexible housing 52b. Thus, fluid expelled from tube 66b will strike the conical surface of baffle 90b so that the fluid will flow down inside walls of housing 52b in a smooth sheet, in the same manner as previously described. The fluid will then be filtered by the filter membrane 102b and will then pass through the openings 130 between the finger-like extensions 128 (see FIG. 11) of outlet tube 106b, from whence it will pass through tube 106b and into the fluid delivery system.

When it is desired to release air bubbles which may be entrapped beneath the filter membrane 102b, the outlet tube 106b may be grasped and the bottom portion 82b of flexible housing 52b may be pushed inwardly in the same manner as described in connection with the embodiment of FIGS. 1–5. When outlet tube 106b is pushed inwardly, the flared portion 124 of stem 126 will be unseated with respect to ring 118 of the filter membrane carrier assembly 100b that is permanently bonded to the annular shoulder 88b of housing 52b. Thus, entrapped air bubbles will be permitted to escape through the opening provided at ring 118 after which the stem 126 of baffle 90b may be returned to its original position in order to form a fluid-tight seal between the flared upper portion 124 of stem 126 and ring 118.

As shown by the foregoing examples, the invention may be embodied in a variety of specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. An improved drip chamber comprising:
   a housing having a fluid inlet, a fluid outlet, and walls defining a chamber;
   means for deflecting incoming fluid from said outlet so as to reduce turbulence of the incoming fluid;
   a filter membrane carrier assembly positioned over said fluid outlet, said filter membrane carrier assembly having a means for filtering said fluid; and
   means for displacing at least a portion of said filter membrane carrier assembly to release entrapped air bubbles from beneath said means for filtering said fluid.

2. An apparatus as defined in claim 1 wherein said entire housing is constructed of flexible plastic material.

3. An apparatus as defined in claim 1 wherein said means for deflecting said fluid comprises a conically-shaped baffle which presents a convex surface positioned beneath said fluid inlet.

4. An apparatus as defined in claim 1 wherein said means for deflecting said fluid comprises a flat baffle oriented at an angle beneath said fluid inlet.

5. An apparatus as defined in claim 3 or 4 wherein said baffle comprises a plurality of radially spaced flanges which extend outward to engage the interior wall of said housing.

6. An apparatus as defined in claim 1 wherein the lower portion of said housing is interiorily shaped to provide a seat for a portion of said filter membrane carrier assembly.

7. An apparatus as defined in claim 6 wherein the lower portion of said housing further comrises a deformable, resilient portion connected to said filter membrane carrier assembly so as to bias said filter membrane carrier assembly against said seat.

8. An apparatus as defined in claim 1 wherein said filter membrane carrier assembly comprises a framework configured as a truncated cone having a seat in the upper portion thereof and a filter membrane supported on said framework, and wherein said means for displacing said filter membrane carrier assembly to release said entrapped air bubbles comprises a stem attached to said means for deflecting said fluid from said inlet, said stem having a flared portion configured to engage said seat, and said stem being displaceable through the upper portion of said framework in order to release air bubbles entrapped within said filter membrane when said stem is displaced upwardly.

9. An apparatus as defined in claim 8 wherein the lower portion of said housing further comprises a deformable, resilient portion connected to said stem so as to bias said stem against said seat.

10. An improved drip chamber for use in a fluid delivery system for administering parenteral fluids to a patient, said drip chamber comprising:
a housing;
an inlet in fluid communication with said housing;
a baffle positioned within said housing adjacent said fluid inlet;
an outlet in fluid communication with said housing;
a filter membrane carrier assembly positioned over said fluid outlet and said filter membrane carrier assembly having a means for filtering said fluid; and
means for displacing said filter membrane carrier assembly to release entrapped air bubbles from beneath said means for filtering said fluid.

11. An apparatus as defined in claim 10 wherein said baffle presents an essentially convex surface positioned beneath said fluid inlet.

12. An apparatus as defined in claim 10 wherein said baffle presents an angularly oriented, essentially planar surface positioned beneath said fluid inlet.

13. An apparatus as defined in claim 10 wherein said housing is interiorly shaped to provide a seat for said filter member carrier assembly, and wherein said means for displacing said filter membrane carrier assembly to release entrapped air bubbles further comprises means for momentarily displacing said filter membrane carrier assembly so that said filter membrane carrier assembly is unseated from said seat.

14. An apparatus as defined in claim 13 wherein the lower portion of said housing further comprises a resilient portion connected to said filter membrane carrier assembly so as to bias said filter membrane carrier assembly against said seat.

15. An apparatus as defined in claim 10 wherein said filter membrane carrier assembly comprises a framework configured as a truncated cone having a seat in the upper portion thereof and a filter membrane supported on said framework, and wherein said means for displacing said filter membrane carrier assembly to release said entrapped air bubbles comprises a stem attached to said baffle, a portion of said stem being configured to engage said seat, said stem being displaceable through said framework so as to momentarily unseat said stem from said seat.

16. An apparatus as described in claim 15 wherein the lower portion of said housing further comprises a resilient portion connected to said stem so as to bias said stem against said seat.

17. An improved drip chamber for use in a fluid delivery system for administering parenteral fluids to a patient, said drip chamber comprising:
a housing having a fluid inlet, a fluid outlet and walls defining a chamber wherein at least the lower portion of said walls are made of a resilient plastic, said housing being interiorily shaped to provide an annular seat in the lower portion thereof;
a baffle positioned beneath said fluid inlet having a plurality of radially spaced flanges which extend outward to engage said walls;
a filter positioned across said fluid outlet and configurated to engage said seat; and
a filter carrier connected to said filter, said carrier comprising an outlet tube connected to said resilient wall portion so that said filter carrier is biased by said resilient wall portion such that said filter engages said seat, and wherein said filter and filter carrier are displaceable so as to momentarily unseat said filter from said seat.

18. An improved drip chamber for use in a fluid delivery system for administering parenteral fluids to a patient, said drip chamber comprising:
a housing having a fluid inlet, a fluid outlet and walls defining a chamber wherein at least the lower portion of said walls are made of a resilient plastic, said housing being interiorly shaped to provide an annular seat in the lower portion thereof;
a baffle positioned beneath said fluid inlet;
a filter positioned across said fluid outlet, said filter comprising a framework configurated as a truncated cone having a seat in the upper portion thereof and a filter membrane supported on said framework; and
a stem attached to said baffle, said stem having a portion configurated to engage said seat, and wherein said stem is biased by said resilient wall portion such that said stem engages said seat, and wherein said stem and said baffle are displaceable so as to momentarily unseat said stem from said seat.

* * * * *

UNITED STATES PATENT AND TRADEMARK OFFICE
CERTIFICATE OF CORRECTION

PATENT NO. : 4,395,260
DATED : July 26, 1983
INVENTOR(S) : Robert J. Todd, et al.

It is certified that error appears in the above—identified patent and that said Letters Patent is hereby corrected as shown below:

Column 1, line 49 should read:

in some cases may even result in death. Thus the prob-

Column 7, line 1 should read:

5. An apparatus as defined in claims 3 or 4 wherein

Column 7, line 53, should read:

filter membrane carrier assembly, and wherein said means

Signed and Sealed this

Twentieth Day of December 1983

[SEAL]

Attest:

Attesting Officer

GERALD J. MOSSINGHOFF
Commissioner of Patents and Trademarks